United States Patent
Teles et al.

Patent Number: 6,060,035
Date of Patent: May 9, 2000

[54] ADDITION REACTION OF HYDROXYL-CONTAINING COMPOUNDS WITH ALKYNES OR ALLENES

[75] Inventors: Joaquim Henrique Teles, Altrip; Norbert Rieber, Mannheim; Klaus Breuer, Altrip; Dirk Demuth, Mannheim; Hartmut Hibst, Schriesheim; Alfred Hagemeyer, Rheine, all of Germany

[73] Assignee: BASF Aktiengesellschaft, Ludwigshafen, Germany

[21] Appl. No.: 09/092,058

[22] Filed: Jun. 5, 1998

[30] Foreign Application Priority Data

Jun. 23, 1997 [DE] Germany .......................... 197 26 670

[51] Int. Cl.[7] .......................... C01B 33/20; C01B 15/14
[52] U.S. Cl. .......................... 423/326; 423/325; 423/324; 423/99
[58] Field of Search .................. 423/326, 325, 423/324, 99

[56] References Cited

U.S. PATENT DOCUMENTS

| | | | |
|---|---|---|---|
| 3,954,937 | 5/1976 | Bodson | 423/326 |
| 4,681,749 | 7/1987 | Usui et al. | 423/326 |
| 5,342,876 | 8/1994 | Abe et al. | 423/326 |

FOREIGN PATENT DOCUMENTS 887330  12/1998  European Pat. Off. .

*Primary Examiner*—Louise N. Leary
*Attorney, Agent, or Firm*—Oblon, Spivak, McClelland, Maier & Neustadt, P.C.

[57] ABSTRACT

Compounds of the formulae I and II

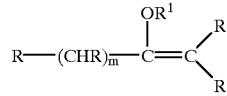

I

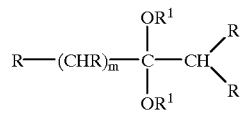

II are prepared by an addition reaction of a compound of the formula III $$R^1OH \qquad \qquad III$$

with an acetylene or allene of the formula IV or V

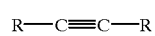

IV

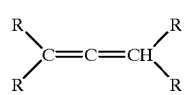

V where $R^1$ and R are as defined, in the gas phase at elevated temperatures in the presence of a heterogeneous, silicate-containing catalyst, by a process in which the catalyst used is one which contains or consists of, as the active component, a zinc silicate obtained by precipitation in aqueous solution from a soluble silicon compound and zinc compound, zinc silicate being a) an essentially X-ray amorphous zinc silicate of the formula VI $$Zn_aSi_cO_{a+2c-0.5e}(OH)_e \cdot fH_2O \qquad \qquad VI,$$

where e is from 0 to 2a+4c and the ratio a:c is from 1 to 3.5, and the ratio f:a is from 0 to 200, and/or b) a crystalline zinc silicate having the structure of hemimorphite of the formula $Zn_4Si_2O_7(OH)_2 \cdot H_2O$.

17 Claims, 2 Drawing Sheets

FIG.1

FIG.2

ADDITION REACTION OF HYDROXYL-CONTAINING COMPOUNDS WITH ALKYNES OR ALLENES

The present invention relates to a process for the addition reaction of hydroxyl-containing compounds with alkynes or allenes with formation of aldehydes and ketones or derivatives thereof in the form of enol ethers or acetals or ketals in the presence of an X-ray amorphous zinc silicate catalyst and/or a crystalline zinc silicate catalyst having essentially the composition or the structure of hemimorphite. The present invention furthermore relates to a novel process for the preparation of such an X-ray amorphous zinc silicate and the catalyst thus obtained and a process for the preparation of a catalyst having the structure of hemimorphite.

The addition reaction of hydroxyl-compounds with alkynes or allenes is almost without exception carried out using homogeneously dissolved catalysts, for example with acids, bases and transition metal complexes (cf. Houben-Weyl, Methoden der organischen Chemie, vol. 6/3, page 233, page 90, vol. 5/2a, page 738, vol. 6/1d, page 136, and vol. 7/a, page 816).

The acid catalysis is generally limited to the addition reaction with activated, electron-rich alkynes (such as acetylene ethers, R—C≡C—OR', acetylene thioethers, R—C≡C—SR', and acetyleneamines, R—C≡C—NR'$_2$).

Under base catalysis (in the presence of KOH or an alcoholate), alcohols can also be subjected to an addition reaction with unactivated alkynes in the liquid phase. This is the most commonly used method; however, the reaction requires high temperatures and pressures, and the space-time yield is relatively low. Typically, a residence time of from 6 to 10 hours at about 160° C. and from 18 to 20 bar is required for the base-catalyzed vinylation of an alcohol.

The addition reaction can also be catalyzed by transition metal complexes in the liquid phase. Mercury(II) or gold(I) salts are particularly suitable for the addition reaction of alcohols while zinc and cadmium salts are preferred for the addition reaction of carboxylic acids and phenols.

The addition reaction of carboxylic acids (in particular acetic acid and propionic acid) with acetylene can also be carried out in the gas phase in the presence of, as catalysts, appropriate zinc carboxylates (including basic zinc carboxylates according to CH 239 752) on carriers having a large surface area.

Finally, the addition reaction of methanol with propyne or propadiene in the gas phase in the presence of zinc oxide on activated carbon or silica gel has also been described in DD 265 289 and that in the presence of zinc nitrate on activated carbon or silica gel in DD 267 629.

All these prior art processes have disadvantages. They either have only a limited field of use or, like the base-catalyzed addition reaction, require high pressures and temperatures, which may lead to safety problems, or they have only a low space-time yield. Homogeneously dissolved transition metal catalysts are often deactivated after a small number of cycles and are furthermore difficult to recycle. Heterogeneous catalysts for the addition reaction of alkynes or allenes have only rarely been described to date. Zinc carboxylates or cadmium carboxylates on activated carbon catalyze only the addition reaction of carboxylic acids (eg. acetic acid or propionic acid) with acetylene. The above-mentioned catalyst based on zinc oxide on activated carbon or silica gel (DD 265 289) is capable of catalyzing the addition reaction of alcohols (methanol or ethanol) with propyne or propadiene with good selectivity (from 90 to 96%) but the catalytic activity is relatively low and the required reaction temperatures are high and required contact times long. At the same temperature, zinc nitrate on activated arbon or silica gel is about an order of magnitude less active than zinc oxide and the selectivity is much lower (max. 70%).

It is an object of the present invention to provide a heterogeneous catalyst for the addition reaction of hydroxyl-containing compounds with alkynes, allenes or mixtures thereof, which catalyst is very active and selective at low temperatures.

We have found that this object is achieved, according to the invention, by a process for the preparation of compounds of the formulae I and II where $R^1$ is hydrogen or an aliphatic, cycloaliphatic, araliphatic, aromatic or heterocyclic radical or an acyl radical, it being possible for these radicals to carry further substituents which do not react with acetylenes or allenes, the radicals R, independently of one another, are hydrogen or aliphatic, cycloaliphatic, araliphatic, aromatic or heterocyclic radicals which may be bonded to one another with formation of a ring, and m is 0 or 1, by an addition reaction of a compound of the formula III $$R^1OH \qquad \qquad III$$

with an acetylene or allene of the formula IV or V where $R^1$ and R have the abovementioned meanings, in the gas phase at elevated temperatures in the presence of a catalyst containing zinc silicate, wherein the catalyst used is one which contains or consists of, as the active component, a zinc silicate obtainable by precipitation in aqueous solution from a silicon compound, in particular an alkaline earth metal or alkali metal silicate, and a zinc compound, in particular a zinc salt, zinc silicate being a) an essentially X-ray amorphous zinc silicate of the formula VI $$Zn_aSi_cO_{a+2c-0.5e}(OH)_e \cdot fH_2O \qquad \qquad VI,$$

where e is from 0 to 2a+4c and the ratio a:c is from 1 to 3.5, preferably from 1.5 to 2.8, particularly preferably from 1.9 to 2.3, in particular from 2 to 2.1, and the ratio f:a is from 0 to 200, preferably from 0 to 2.5, particularly preferably from 0 to 0.25, and/or b) a crystalline zinc silicate having essentially the structure of hemimorphite of the formula $Zn_4Si_2O_7(OH)_2 \cdot H_2O$, where zinc may be present in a 25% substoichiometric amount or excess, based on the stoichiometric composition.

The amorphous catalyst (a) to be used according to the invention can also be physically characterized. With the use of Cu-K$\alpha_1$ radiation ($\lambda$=1.5406 Å), it has two broad bands at 2θ=31 ±5° and at 2θ=61±70° in the powder X-ray diffraction pattern.

The zinc silicates to be used according to the invention can furthermore be doped with up to 80, preferably 50, in particular 20, mol percent of further metals selected from the group (A) consisting of beryllium, magnesium, calcium, strontium, barium, manganese, iron, cobalt, nickel, copper, cadmium and mercury and the group (B) consisting of titanium, zirconium, hafnium, germanium, tin and lead, the elements of group (A) replacing some of the zinc and the elements of group (B) replacing some of the silicon in the formula VI. In the case of cadmium, zinc may also be completely replaced by cadmium. However, owing to the toxicity of the cadmium, cadmium silicates have no advantages.

Where the ratio of zinc to silicon is about 2, the catalyst of the formula VI corresponds to the composition of (crystalline) hemimorphite, to which the novel X-ray amorphous zinc silicates of the formula VI may be converted by prolonged heating in aqueous suspension.

Catalysts which may be used as catalysts having the structure of hemimorphite also include those in which the ratio of zinc to silicon is nonstoichiometric, rather those which have up to 25% substoichiometric amount or excess of zinc, corresponding to an atomic Zn:Si ratio of from 1.6 to 2.5. Hemimorphite catalysts which have from 0 to 20%, in particular from 0 to 10%, zinc excess are preferred.

The use of a heterogeneous catalyst which contains, as the active component, at least predominantly zinc silicate having the 40 structure of hemimorphite of the formula $Zn_4Si_2O_7(OH)_{2-2y}O_y \cdot xH_2O$, where x and y are each from 0 to 1, is essential for the reaction according to the invention.

The preparation of hemimorphite is known from the literature. It can be carried out under standard conditions or hydrothermal conditions.

A) Hemimorphite catalyst a) Preparation under standard conditions

A. G. Merkulov and B. S. Khristoforov, (Tr. Soveshch. Eksp. Tekh. Mineral. Petrogr., 8$^{th}$ (1971), Meeting Date 1968, 322–8; Editor(s): V. V. Lapin; Publisher: "Nauka", Moscow, USSR) describe the preparation of various zinc silicates by reacting various zinc salts (carbonate, sulfate, chloride, acetate or oxide) with sodium silicate and sodium hydroxide in aqueous solution at 90–100° C. at atmospheric pressure. Depending on the pH established, various zinc silicates form. For example, pure sauconite having the composition $Zn_3Si_4O_{10}(OH)_2 \cdot nH_2O$ forms at a final pH of 5–6. Pure willemite ($\alpha$-$Zn_2SiO_4$) is precipitated in the pH range of 6.5–8.5. On the other hand, pure hemimorphite ($Zn_4Si_2O_7(OH)_2 \cdot H_2O$) crystallizes only in a weakly alkaline medium at a pH greater than 10.

In another paper by the stated authors (A. G. Merkulov and B. S. Khristoforov, Izv. Sib. Otd. Akad. Nauk SSSR, Ser. Khim. Nauk 4 (1969), 70–4), it is stated that pure hemimorphite is formed on reacting zinc salts with sodium silicate and sodium hydroxide solution at 90–100° C. at atmospheric pressure in aqueous solution only in a pH range of 10–12.

Furthermore, T. Baird, A. G. Cairns Smith and D. S. Snell (Reactivity of Solids, Proc. Int. Symp., 8th (1977), G öteborg, Meeting Date 1976, 337–42; Editor(s): J. Wood, O. Lindqvist and C. Helgesson; Publisher: Plenum Press, New York, N.Y.) were able to prepare large crystals of hemimorphite by reacting $Zn(OH)_2$ with silica and LiOH in aqueous solution at a pH of 10.

Finally, H. Nagata, M. Matsunage and K. Hosokawa (Zairyo-to-Kankyo 42 (1993), 225–233) prepared hemimorphite by reacting aqueous zinc sulfate solution with sodium hydroxide solution and aqueous sodium silicate solution at a pH of 13, isolating the resulting precipitate, washing it thoroughly and aging it at 85° C. for at least 24 hours.

b) Hydrothermal preparation

According to EP 165 647, hemimorphite can be prepared from an acid-treated clay mineral and zinc oxide or zinc hydroxide under hydrothermal conditions (170° C., 5 h). However, the acid pretreatment of the clay is very expensive and this process is therefore disadvantageous.

According to D. M. Roy and F. A. Mumpton (Econ. Geol. 51 (1956), 432–443), hemimorphite can furthermore be obtained by hydrothermal reaction of mixtures of ZnO and $SiO_2$ at 175–200° C. (composition: 3 $ZnO+2SiO_2$). The product obtained contains predominantly hemimorphite but is contaminated with sauconite ($Zn_3Si_4O_{10}(OH)_2 \cdot 4H_2O$).

Finally, P. Taylor and D. G. Owen, (Polyhedron 3 (2) 1984, 151–155) describe the hydrothermal synthesis of hemimorphite by reacting ZnO with $SiO_2$ in aqueous solution at 150° C. However, long reaction times of at least 4 days were required for preparing products having a high hemimorphite content.

Although hemimorphite products obtained by the known methods described above are very suitable as catalysts for the novel addition reaction, it was found that it was desirable to improve their properties further and to propose a preparation method which permits the preparation of catalysts having a reproducibly good property profile.

Accordingly, we have found a novel preparation method, both under atmospheric pressure and under hydrothermal conditions, in which an alkali metal or alkaline earth metal silicate, preferably sodium silicate, is reacted with a zinc salt, in particular zinc nitrate, and a base, such as an alkali metal or alkaline earth metal hydroxide, in particular sodium hydroxide, in aqueous solution at a pH of from 4 to 9.5, preferably from 5.5 to 8, in particular at a pH around the neutral point, for example at pH 6 to 7.5, at from 50 to 100° C., in particular from 70 to 100° C., in the case of atmospheric pressure and at from 100 to 250° C., preferably from 100 to 200° C., in the case of hydrothermal conditions.

In the novel preparation method, pure hemimorphite having a Zn/Si ratio of 2 can be synthesized. However, hemimorphite preparations containing up to 25% less or more than the stoichiometric amount of zinc, equivalent to an atomic Zn:Si ratio of from 1.6 to 2.5, are also obtainable. Preferred catalysts are hemimorphites which have a zinc excess of from 0 to 20%. Hemimorphites which have a zinc excess of from 0 to 10% are particularly preferred.

The hemimorphite products are obtained in the synthesis as a white crystalline precipitate in the form of an aqueous suspension and have to be separated from the aqueous solution by suitable measures, for example filtration or centrifuging. In the case of filtration, the filter cake obtained is then thoroughly washed to free it from soluble salts and is then dried. The drying can be effected at up to 600° C., the preferred temperature range being from 90 to 450° C. Thermogravimetric analyses have shown that the crystallized hemimorphite having the composition $Zn_4Si_2O_7(OH)_2 \cdot H_2O$ loses an increasing proportion of its water of crystallization in the temperature range from about 100 to 200° C. while retaining the hemimorphite structure, resulting in hemimorphite preparations having the composition $Zn_4Si_2O_7(OH)_2 \cdot xH_2O$, where x is less than 1 and decreases with increasing temperature. If drying is carried out in a higher temperature range from about 200 to 600° C., the OH⁻ ions present in the hemimorphite are additionally converted into $O^{2-}$ ions and eliminated $H_2O$ ($2OH^- \rightarrow H_2O + O^{2-}$), likewise with retention of the hemimorphite structure, resulting in hemimorphite preparations having the composition $Zn_4Si_2O_7(OH)_{2-2y}O_y$, where y is from 0 to 1 and increases with increasing temperature.

The hemimorphite preparations obtained after drying at up to 600° C., preferably from 90 to 450° C. and having the composition $Zn_4Si_2O_7(OH)_{2-2y}O_y.xH_2O$, where x and y are from 0 to 1, are then usually processed to catalytic moldings by the conventional shaping methods, for example pelleting or extrusion, or are converted into coated catalysts on steatite beads. Details are described in the examples.

B) X-ray amorphous zinc silicate catalyst

It has now been found that an X-ray amorphous product having improved catalytic properties is obtained essentially under the same preparation conditions but in a shorter reaction time than the precursor for the preparation of a crystalline hemimorphite.

For example, according to the invention an aqueous suspension of an alkali metal or alkaline earth metal silicate is reacted for this purpose with an aqueous solution of a zinc salt at a) from 20° C., preferably 50° C., to the boiling point of the resulting aqueous suspension, at
b) a pH of from 4 to 9.5, preferably at a pH close to the neutral point, and
c) in ratios of alkali metal silicate to zinc salt such that the conditions of the formula VI are fulfilled, and
d) a residence time is maintained such that considerable crystallization of the zinc silicate does not as yet occur.

Figure 2:
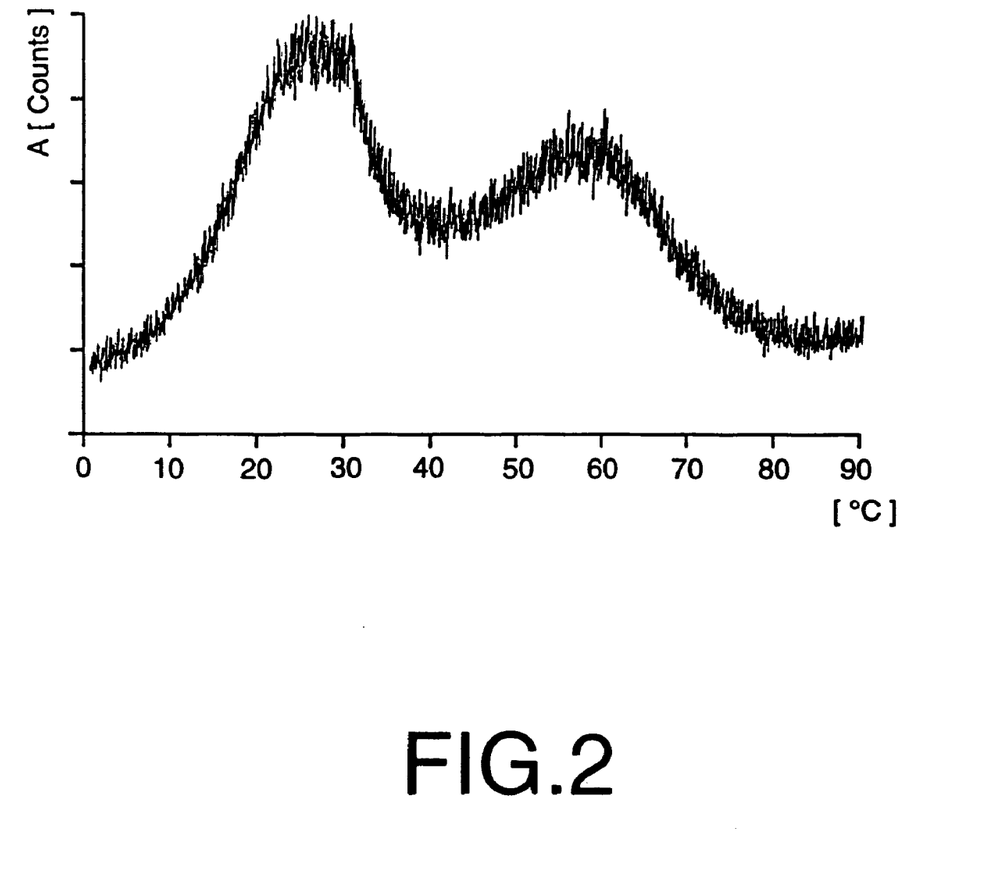

The essentially X-ray amorphous zinc silicate obtainable in this way contains $Zn^{2+}$, $Si^{4+}$ and $O^2$ ions; in addition, the compound may contain OH ions and water of hydration. The Zn/Si ratio is from 0.3 to 5, preferably from 1 to 2.7, particularly preferably from 2 to 2.3, very particularly preferably 2. In the last-mentioned case, the X-ray amorphous zinc silicate thus has the Zn/Si ratio of crystalline hemimorphite ($Zn_4Si_2O_7(OH)_2.H_2O$). The powder X-ray diffraction pattern of the novel X-ray amorphous zinc silicate, obtained using Cu-K$\alpha_1$ radiation ($\lambda=1.5406$ Å), is shown in FIG. 2, the intensity A of the diffracted X-rays being plotted as a function of twice the diffraction angle ($2\theta$). In the $2\theta$ range from 10° to 90°, the powder X-ray diffraction pattern of the novel X-ray amorphous zinc silicate has very broad intensity maxima at $2\theta=31°\pm5°$ and at $2\theta=61°\pm7°$. In FIG. 2, above the stated broad diffraction reflections of the novel X-ray amorphous zinc silicate, there are also sharper lines which can be assigned to the formation of small amounts of crystalline ZnO (index card 5-0664 of the JCPDS-ICDD index (1995)). In addition, small amounts of $Zn_5(NO_3)_2(OH)_8.2H_2O$ may also occur (index card 24-1460 of the JCPDS-ICDD index (1995)).

The novel X-ray amorphous zinc silicate is obtained as a powder in the preparation. This powder can be used as such for the catalytic reaction (for example in a fluidized-bed reactor) or, after molding (for example extrusion, pelleting, etc., possibly also with the addition of assistants) in a form suitable for a fixed-bed reactor.

Before use, the catalyst may be calcined at from 80° C. to 750° C. The catalyst is preferably calcined at from 120° C. to 500° C. Calcination at from 200° to 400° C. in the air is particularly preferred. To increase the pore volume, pore formers (eg. superabsorbers such as Lutexal P® (from BASF AG) or Walocel® (methylcellulose/synthetic resin combination, from Wolff, Walsrode AG)) may also be added during the shaping procedure, for example during pelleting or extrusion.

Suitable starting materials for the novel reaction are any desired alkynes or allenes or mixtures thereof. As a rule, however, industrially readily obtainable acetylenes and allenes of 2 to 8 carbon atoms and of 3 to 8 carbon atoms, respectively, are used. Propyne and allene are particularly preferred, especially hydrocarbon streams which contain them.

The hydroxyl-containing compound $R^1OH$ may be water, any desired alcohol, a phenol or a carboxylic acid. In general, alcohols, in particular alkanols of 1 to 16 carbon atoms, mononuclear phenols and low molecular weight carboxylic acids, for example of 1 to 16 carbon atoms, are especially suitable. Lower alcohols are particularly preferred, especially methanol.

The addition reaction of the hydroxyl-containing compounds is carried out in the presence of the heterogeneous catalyst in the gas phase, either over a fixed bed or in a fluidized bed, at from 50 to 400° C., preferably 100 to 250° C., particularly preferably from 120 to 200° C., and from 0.1 to 100, in particular from 0.8 to 20, bar (all pressures based on the sum of the partial pressures of the starting materials).

If required for operational safety and better heat removal, the reaction mixture may be diluted with inert gases, such as nitrogen, argon, low molecular alkanes or olefins.

The molar ratio of the hydroxyl-containing component to alkyne or allene may be from 0.01 to 100, preferably from 0.1 to 5, particularly preferably from 0.7 to 1.3.

The selectivity of the reaction with respect to the monoadducts and diadducts can be controlled by means of the reaction conditions. Low ratios of hydroxyl-containing component to alkyne or allene at high temperatures and low partial pressures of the reactants lead to preferential formation of the monoadducts, whereas high ratios of hydroxyl-containing component to alkyne or allene at low temperatures and high partial pressures of the reactants promote the formation of the bisadducts. For example, 2-methoxypropene or 2,2-dimethoxypropane can be selectively formed from propyne or allene with methanol, depending on the reaction conditions.

Standard methods are used for characterizing the catalyst samples (fresh samples as well as samples removed from the reactor). The measured BET surface area is as a rule from 50 to 500 m²/g. Catalysts having BET surface areas of from 80 to 400 m²/g are preferably used. Furthermore, the samples obtained by the novel preparation process were investigated by mean of powder X-ray diffractometry (XRD).

General reaction conditions

Figure 1:
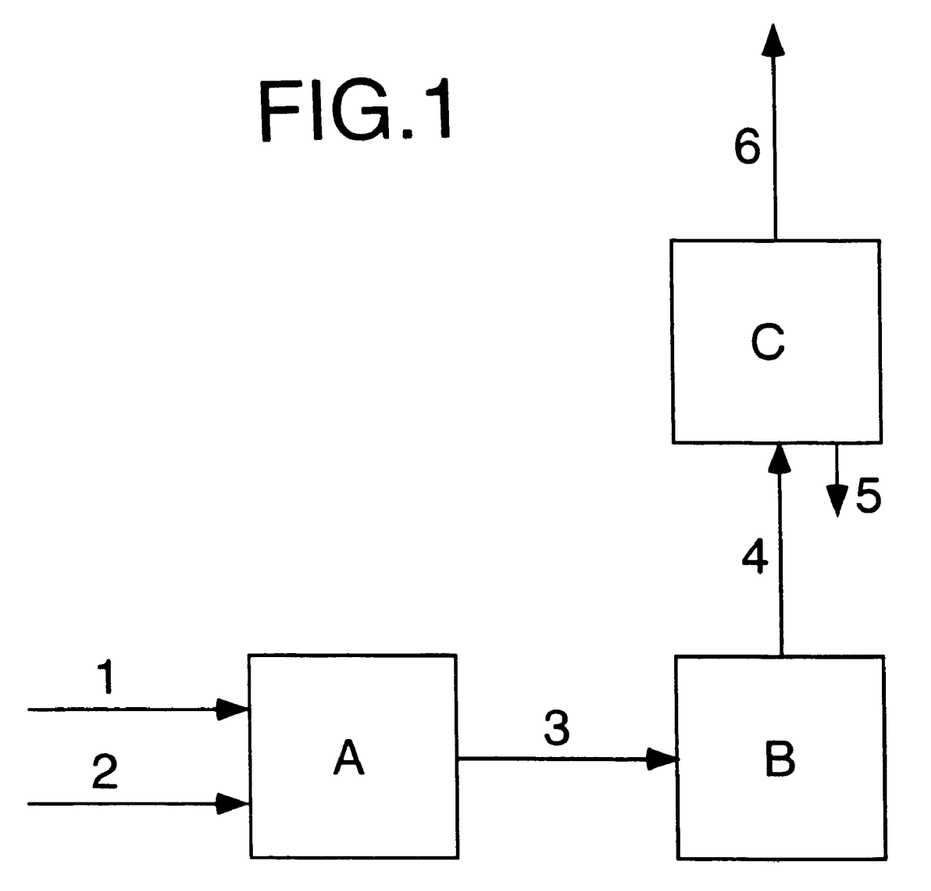

The catalytic reactions according to FIG. 1 were carried out in a gradient-free CSTR (Continuously Stirred Tank Reactor) (A) having a volume of 1740 ml and a catalyst volume of about 90 ml, modified for heterogeneous gas-phase reactions. The reactor had an internal diameter of about 108 mm and a height of about 200 mm and was heated by means of an electrical heating coil mounted on the inner surface. A small metal cylinder (diameter about 64 mm, height about 150 mm) was mounted in the center of the reactor and was provided at half height (about 85 mm below the upper edge) with a wire grid. The catalyst was loosely poured onto this wire grid. A flat turbine (diameter about 100 mm, height about 20 mm) was mounted on the reactor cover and was driven at 1500–2000 rpm. A total of 6 thermocouples for temperature monitoring were mounted at various heights along the reactor axis. The starting materials were metered in under pressure by means of HPLC pumps, mixed shortly before the reactor and let down into the reactor space.

The alkyne and allene (1 in FIG. 1) were metered in either in pure form or as a mixture diluted with other inert components. In the case of propyne and allene, a mixture with other hydrocarbons was used (composition: 30–43% by volume of propyne, 16–20% by volume of allene 20–45% by volume of propene, 5–10% by volume of isobutane and 2–6% by volume of propane as main components; all other components less than 1%. This mixture was obtained by distillation from a side stream of a steam cracker). About 10% by weight of cyclohexane as an internal standard for GC analysis were metered into the alcohol component.

The reaction was carried out isothermally at from 120 to 300° C. and with a feed rate from 0.5 to 10 mmol/min of propyne and/or allene and from 0.5 to 20 mmol/min of methanol. The reaction pressure was from 1.1 to 3.5 bar (absolute).

The total amount of gas, consisting of starting materials, inert gas and internal standard, was as a rule from 4 to 60 l (s.t.p.)/h. The GHSV (gas hourly space velocity), which is defined as $$GHSV = \text{gas volume}[1(s.t.p.)/h]/\text{catalyst volume} \quad [1],$$

was from 80 to 1200 $h^{-1}$. The LHSV (liquid hourly space velocity), which is defined as
LHSV=liquid volume[1(s.t.p.)/h]/catalyst volume [1] (in this case transported volume of propyne and volume of methanol),
was from 0.2 to 3 $h^{-1}$. The residence time, defined as a quotient of the catalyst volume [1] and the amount of gas [1(s.t.p.)/s], was from 3 to 40 s.

After leaving the reactor, the reaction gases were fed via a heated transfer line (3) to an on-line gas chromatograph (B) and were analyzed there every 2 hours. Thereafter, the gas stream was subjected to a partial condensation (C) and the fraction (6) which was not condensable at room temperature was analyzed at regular intervals (about 12 hours) by means of off-line GC. The condensate (5) was likewise collected and was analyzed by means of off-line GC.

The enol ethers of the formula I which were obtainable according to the invention and the dialkoxy compounds of the formula II are useful intermediates for the preparation of active ingredients and fragrances. In particular, the enol ethers are desirable starting materials, for example for the preparation of γ,δ unsaturated ketones as intermediates for the preparation of isophytol.

If it is intended to obtain in particular the enol ethers, the compounds of the formula II can be converted in a manner known per se into the corresponding enol ethers of the formula I by elimination of one mole of $R^1OH$. Many processes disclosed in DE-A-35 35 128, D -A-37 22 891, DE-A-38 04 162, Chemical Abstracts, Vol. 9, (19), 156 241 f, and DE-A-19544450 exist for this purpose.

EXAMPLE 1

Preparation of $Zn_4Si_2O_7(OH)_2 \cdot H_2O$ with Zn/Si=2 (stoichiometric hemimorphite) and catalytic reaction In an 8 l stirred container, a suspension A containing 1.5 mol of $SiO_2$ and 0.89 mol of Na was prepared from 4.5 l of demineralized water and 145.1 g of soda waterglass powder having an $SiO_2$ content of 62.1% by weight and an $Na_2O$ content of 19.0% by weight (from Riedel-de Haen, D-30918 Seelze). Furthermore, 910.7 g of $Zn(NO_3)_2 \cdot 6H_2O$ (98% strength) were dissolved in 2.25 l of demineralized water at room temperature, a solution B containing 3 mol of Zn and 6 mol of $NO_3$ being obtained. Finally, an aqueous solution was prepared from 204.4 g of NaOH in 225 ml of demineralized water, a solution C having an Na content of 5.11 mol being obtained. The solutions B and C were then added at room temperature to the suspension A, resulting in a milky suspension D having the following proportions of elements: Zn content=3 mol, Si content=1.5 mol, Na content=6 mol, $NO_3$ content=6 mol. The pH of the suspension D obtained was 7.1. The suspension D was heated to 90° C. and stirred for 24 hours at a speed of 200 rpm at this temperature. The suspension was then cooled to room temperature, and a final pH of 7.0 was measured. The white precipitate which crystallized out was filtered off and washed Na-free with demineralized water, and the resulting filter cake was dried at 90° C. in a drying oven. The dried white powder was investigated by X-ray diffraction, resulting in a powder X-ray diffraction pattern which corresponded completely to that of index card 5-0555 of the JCPDS-ICDD index (1995) and thus proved the preparation of $Zn_4Si_2O_7(OH)_2 \cdot H_2O$. The specific surface area of the resulting powder, determined according to BET, was 30 $m^2/g$.

For the preparation of a catalyst, the still moist powder was directly extrude (diameter=3 mm, pressure=50 bar) and the extrudates were then dried for 16 hours at 120° C. The prepared catalyst had a BET surface area of 26 $m^2/g$ and a hardness of 6 N/molding.

About 90 ml of the catalyst were introduced into the apparatus described under (a), and the propyne/allene mixture (about 63% strength by volume, 2.8 mmol/min) and methanol (4.7 mmol/min; total feed with inert substances: 9.4 mmol/min; methanol/(propyn+allene) ratio=1.68) were then metered in by means of HPLC pumps. The reaction temperature was 200° C. and the pressure 1.25 bar (partial pressure of the starting materials: 1.0 bar). The following selectivities were observed from the beginning (ie. the catalyst had no formation time): 2-methoxypropene=91%; 2,2-dimethoxypropane=5%; acetone=1%; cis- and trans-1-methoxypropene=3%. The propyne/allene conversion was 48%. The following values were determined for the catalyst after removal from the reactor: BET=25 $m^2/g$, hardness=6 N/molding.

EXAMPLE 2

Preparation of hemimorphite catalyst with Zn/Si=2.2 and catalytic reaction

In a 6 l stirred container, a suspension A containing 1.0 mol of $SiO_2$ and 0.59 mol of Na was prepared from 3.0 l of demineralized water and 96.8 g of soda waterglass powder having an $SiO_2$ content of 62.1% by weight and an $Na_2O$ content of 19.0% by weight (from Riedel-de Haen, D-30918 Seelze) and a solution B containing 2.2 mol of Zn and 4.4 mol of $NO_3$ was prepared from 667.8 g of $Zn(NO_3)_2 \cdot 6 H_2O$ (98% strength) in 1.5 l of demineralized water at room temperature and an aqueous solution C having an Na content of 3.81 mol was prepared from 152.3 g of NaOH in 400 ml of demineralized water. The solutions B and C were added to the suspension A at room temperature, resulting in a milky suspension D having the following proportions of elements: Zn content=2.2 mol, Si content=1 mol, Na content=4.4 mol, $NO_3^-$ content=4.4 mol. The pH of the suspension D obtained was 7.2. The suspension D was heated to 90° C. and stirred at this temperature for 24 hours at a speed of 200 rpm. After the suspension had been cooled to room temperature, a final pH of 7.0 was measured. The resulting white precipitate was filtered off and washed Na-free with demineralized water, and the filter cake obtained was dried at 90° C. in a drying oven.

The dried white powder was analyzed by X-ray diffraction, resulting in a po der X-ray diffraction pattern which completely corresponded to that of index card 5-0555 of the JCPDS-ICDD index (1995) and thus indicated the preparation of $Zn_4Si_2O_7(OH)_2.H_2O$. The specific surface area of the resulting powder, determined according to BET, was 60 $m^2/g$.

650 g of the powder were mixed with 20.2 g of magnesium stearate (Merck) and the mixture was compressed to give 20 mm pellets. These pellets were crushed to give chips (<0.5 mm) and the chips were processed to give annular pellets (5×5×2 mm). The pellets were then calcined for 10 hours at 350° C. The prepared catalyst had a BET surface area of 44 $m^2/g$ and a hardness of 44 N/molding.

About 90 ml of the catalyst were introduced into the apparatus described under (a) and the propyne/allene mixture (about 60% strength by volume, 2.8 mmol/min) and methanol (2.0 mmol/min; total feed with inert substances: 6.8 mmol/min; methanol/(propyne+allene) ratio=0.72) were metered in by means of HPLC pumps. The reaction temperature was 170° C. and the pressure 1.1 bar (absolute (partial pressure of the starting materials: 0.8 bar). The following selectivities were observed from the beginning (ie. the catalyst had no formation time): 2-methoxypropene= 90%; 2,2-dimethoxypropane=3%; acetone=2%; cis- and trans-1-methoxypropene=2%. The propyne/allene conversion was 71 and the methanol conversion 98%.

The following physical properties were determined for the catalyst after removal from the reactor: BET=44 $m^2/g$; hardness=12 N/molding.

EXAMPLE 3

Hydrothermal prep ration of $Zn_4Si_2O_7(OH)_2.H_2O$ with Zn/Si=2 and catalytic reaction In a 2 l stirred container, a suspension A containing 0.2 mol of $SiO_2$ and 0.12 mol of Na was prepared from 200 ml of demineralized water and 19.35 g of soda waterglass powder having an $SiO_2$ content of 62.1% by weigh and an $Na_2O$ content of 19.0% by weight (from Riedel-de Haen, D-30918 Seelze) and a solution B containing 0.4 mol of Zn and 0.8 mol of $NO_3$ was prepared from 121.4 g of $Zn(NO_3)_2.6H_2O$ (98% strength) in 200 ml of demineralized water at room temperature and an aqueous solution C having an Na content of 0.68 mol was prepared from 27.2 g of NaOH in 100 ml of demineralized water. The solutions B and C were added to the suspension A at room temperature, resulting in a milky suspension D having the following proportions of elements: Zn content=0.4 mol, Si content=0.2 mol, Na content=0.8 mol, $NO_3^-$ content=0.8 mol. The pH of the suspension D obtained was 7.0. The suspension D was heated to 150° C. in an autoclave made of a Hastelloy alloy and having an internal volume of 1.2 l and was stirred for 6 hours at this temperature at a speed of 200 rpm, a gauge pressure of 7 bar being measured. After the-resulting suspension had been cooled to room temperature, a final pH of 7.2 was measured. The resulting white precipitate which crystallized out was filtered off and washed Na-free with demineralized water, and the filter cake obtained was dried at 90° C. in a drying oven.

The powder X-ray diffraction pattern of the dried white powder corresponded to that of index card 5-0555 of the JCPDS-ICDD index (1995) and proved the preparation of $Zn_4Si_2O_7(OH)_2.H_2O$. The specific surface area of the resulting powder, determined according to BET was 28.7 $m^2/g$.

150 g of steatite beads (diameter=2 mm) were coated on a turntable with 19.2 g of a 1.25% strength by weight aqueous solution of Walocel® (from Wolff, Walsrode), 5.60 g of the $Zn_4Si_2O_7(OH)_2.H_2O$ powder and 8.70 g of zinc powder. After drying (4 hours at 120° C.), a coated catalyst was obtained.

About 90 ml of the catalyst were introduced into the apparatus described under (a) and the propyne/allene mixture (about 61% strength by volume, 3.0 mmol/min) and methanol (4.7 mmol/min; total feed with inert substances: 9.7 mmol/min; methanol/(propyne+allene) ratio=1.59) were metered in by means of HPLC pumps. The reaction temperature was 200° C. and the pressure 1.25 bar (absolute) (partial pressure of the starting materials: 1.0 bar). The propyne/allene conversion was constant from the beginning and was about 17%. The following products formed (selectivities in brackets): 2-methoxypropene (90%), 2,2-dimethoxypropane (3%) and cis- and trans-1-methoxypropene (6%).

EXAMPLE 4

(Comparative Example)

Preparation of $\beta$-$Zn_2SiO_4$ catalyst (Zn/Si=2) and catalytic reaction 100 g of the hemimorphite prepared according to Example 1 were heated for 1 hour at 700° C. in an oven. The powder obtained was analyzed by X-ray diffraction, resulting in a powder X-ray diffraction pattern which completely corresponded to that of index card 14-065 of the JCPDS-ICDD index (1995) and thus indicated the formation of $\beta$-$Zn_2SiO_4$ as a pure phase. The specific surface area of the resulting white powder, determined according to BET, was 25 $m^2$ g.

150 g of steatite beads (diameter 2 mm) were coated on a turntable with 17.2 g of a 1.25% strength by weight aqueous solution of Walocel® (from Wolff, Walsrode), 5.50 g of the $\beta$-$Zn_2SiO_4$ powder and 5.50 g of zinc powder. After drying (4 hours at 120° C.) a coated catalyst was obtained.

About 90 ml of the catalyst were introduced into the apparatus described under (e) and the propyne/allene mixture (about 63% strength by volume, 3.1 mmol/min) and methanol (3.9 mmol/min; total feed with inert substances: 9.0 mmol/min; methanol/(propyne+allene) ratio=1.25) were metered in by means of HPLC pumps. The reaction temperature was 200° C. and the pressure 1.2 bar (absolute). The propyne/allene conversion was less than 1% and furthermore did not increase with time.

EXAMPLE 5

(Comparative Example)

Preparation of $\alpha$-$Zn_2SiO_4$ catalyst (willemite) and catalytic reaction 100 g of the hemimorphite prepared according to Example 1 were heated for 1 hour at 800° C. in an oven. The resulting powder was analyzed by X-ray diffraction, resulting in a powder X-ray diffraction patter which completely corresponded to that of index card 37-1485 of the JCPDS-ICDD index (1995) and thus indicated the preparation of $\alpha$-$Zn_2SiO_4$ (willemite) as a single phase. The specific surface area of the resulting white powder, determined according to BET, was 18 $m^2/g$.

The powder was mixed with 2% by weight of graphite and 3% by weight of magnesium stearate and compressed to give 3×5 mm pellets. These pellets had a BET surface area of 0.6 $m^2/g$.

About 90 ml of the catalyst were introduced into the apparatus described under (a) and the propyne/allene mixture (about 62% strength by volume, 3.3 mmol/min) and methanol (4.0 mmol/min; total feed with inert substances: 9.5 mmol/min; methanol/(propyn+allene) ratio=1.21) were metered in by means of HPLC pumps. The reaction temperature was 200° C. and the pressure 1.25 bar (absolute). The propyne/allene conversion was less than 1% and furthermore did not increase with time.

EXAMPLE 6

(Comparative Example)
Preparation of $Zn_3Si_4O_{10}(OH)_2.4H_2O$ catalyst (sauconite) and catalytic reaction In a 6 l stirred container, a suspension A containing 6 mol of $SiO_2$ and 3.56 mol of Na was prepared from 3 l of demineralized water and 580.5 g of soda waterglass powder having an $SiO_2$ content of 62.1% by weight and an $Na_2O$ content of 19.0% by weight (from Riedel-de Haen, D-30918 Seelze) and a solution B containing 2 mol of Zn and 4 mol of $NO_3^-$ was prepared from 607.1 g of $Zn(NO_3)_2.6H_2O$ (98% strength in 1.5 l of demineralized water at room temperature and a aqueous solution C having an Na content of 0.44 mol was prepared from 17.6 g of NaOH in 200 ml of demineralized water. The solutions B and C were added to the suspension A at room temperature, resulting in a milky suspension D having the following proportions of elements: Zn content=2 mol, Si content=6 mol, Na content=4.0 mol, $NO_3^-$ content=4 mol. The pH of he suspension D obtained was 6.8. The suspension D was heated to 90° C. and stirred at this temperature for 24 hours at a speed of 200 rpm. After the resulting suspension had been cooled to room temperature, a final pH of 6.9 was measured. The resulting white precipitate was filtered off and washed Na-free with demineralized water, and the filter cake obtained was dried at 90° C. in a drying oven.

The powder X-ray diffraction pattern of the dried powder showed that it corresponds to index card 29-1393 of the JCPDS-ICDD index (1995) and hence $Zn_3Si_4O_{10}(OH)_2.4H_2O$ (sauconite). The specific surface area of the resulting white powder, determined according to BET, was 216 $m^2/g$.

150 g of steatite beads (diameter=2 mm) were coated on a turntable with 17 5 g of a 1.25% strength by weight aqueous solution of Walocel® (from Wolff, Walsrode) and a mixture of 10.2 g of zinc po der and 6.9 g of sauconite. The catalyst was then dried for 4 ours at 120° C. in the air.

About 90 ml of the catalyst were introduced into the apparatus described above. The propyne/allene mixture (about 63% strength by volume, 3.8 mmol/min) and methanol (4.7 mmol/min; total feed with inert substances: 11.0 mmol/min; methanol/(propyne+allene) ratio=1.25) were then metered in by means of HPLC pumps. The reaction temperature was 200° C. and the pressure 1.25 bar (absolute). The propyne/allene conversion was less than 1% and furthermore did not increase with time.

EXAMPLE 7

Preparation of X-ray amorphous zinc silicate having a molar Zn/Si ratio of 2.1 (corresponds to a 5% excess, based on the composition $Zn_4Si_2O_7(OH_2).H_2O$)

48.37 g of soda waterglass powder having an $SiO_2$ content of 62.1% by weight and an $Na_2O$ content of 19.0% by weight (from Riedel-de Haen, D-30918 Seelze) were added to 3.0 l of demineralized water at 65° C. in a 6 l stirred container with continuous stirring (100 rpm), a suspension A containing 0.5 mol of $SiO_2$ and 0.3 mol of Na being obtained. Furthermore, an aqueous solution B of 72.16 g of NaOH (1.8 mol) in 0.2 l of demineralized water was prepared. Finally, 318.7 g of $Zn(NO_3)_2.6H_2O$ (98% strength) were dissolved in 1.5 l of demineralized water, a solution C containing 1.05 mol of Zn and 2.1 mol of $NO_3^-$ being obtained. The solution B was then added to the suspension A at 65° C., a clear solution D being obtained after about 5 minutes. The solution C was then added to the resulting solution D. A white suspension E having a Zn content of 1.05 mol, an Si content of 0.5 mol, an Na content of 2.1 mol and an $NO_3^-$ content of 2.1 mol was formed. The suspension E was heated at 65° C. for 2 hours while stirring (100 rpm) and then cooled to room temperature. After cooling, a final pH of 6.6 was measured. The resulting white precipitate was filtered off, and washed Na-free with demineralized water, and the filter cake obtained was dried at 80° C. in a drying oven.

The dried white powder was analyzed by X-ray diffractometry using Cu-$K\alpha_1$ radiation ($\lambda$=1.5406 Å) in the $2\theta$ range from 10° to 90°, resulting in a powder X-ray diffraction pattern (the intensity A of the diffracted X-rays plotted as a function of twice the diffraction angle ($2\theta$)) which is shown in FIG. 2 and which indicates the formation of predominant amounts of the novel X-ray amorphous zinc silicate in addition to a small amount of crystalline ZnO (index card 5-0664 of the JCPDS-ICDD index (1995)). The powder X-ray diffraction pattern shown in FIG. 2 was resolved into a super position of separate diffraction reflections with the aid of the software package DIFFRAC-AT V 3.2/PROFILE, Pearson-VII form function, 1994 version (from Siemens) under the boundary conditions of a minimum mean square deviation, on the one hand the reflections of the ZnO present as a secondary component and on the other hand the broad reflections of the novel X-ray amorphous zinc silicate being taken into account. Measurement of the powder X-ray diffraction pattern of the novel X-ray amorphous zinc silicate resolved in this manner lead to intensity maxima at $2\theta=31°\pm5°$ and at $2\theta=61°\pm7°$. The specific surface area of the resulting powder, determined according to BET was 124.0 $m^2/g$.

EXAMPLE 8

Preparation of X ray amorphous zinc silicate having the composition $Zn_4Si_2O_7(OH)_2.H_2O$ with Zn/Si=2.1; corresponding to 5% Zn excess)

120.93 g of soda waterglass powder having an $SiO_2$ content of 62.1% by weight and an $Na_2O$ content of 19.0% by weight (from Riedel-de Haen, D-30918 Seelze) were added to 7.5 l of demineralized water at 80° C. in a 12 l stirred container with continuous stirring (100 rpm), a suspension A containing 1.25 mol of $SiO_2$ and 0.74 mol of Na being obtained. Furthermore, an aqueous solution B of 180.4 g of NaOH (4.51 mol) in 0.5 l of demineralized water was prepared. Finally, 796.0 g of $Zn(NO_3)_2.6H_2O$ were dissolved in 2.5 l of demineralized water, a solution C containing 2.625 mol of Zn and 5.25 mol of $NO_3^-$ being obtained. The solution B was then added to the suspension A at 80° C., a clear solution D being obtained after about 5 minutes. The solution C was then added to the resulting solution D. A white suspension E having a Zn content of 2.625 mol, an Si content of 1.25 mol, an Na content of 5.25 mol and an $NO_3^-$ content of 5.25 mol was formed. The suspension E was heated at 80° C. for 2 hours while stirring (100 rpm) and then cooled to room temperature. After cooling, a final pH of 6.5 was measured. The resulting white precipitate was filtered off, and washed Na-free with demineralized water, and the filter cake obtained was dried at 80° C. in a drying oven.

The dried white powder was analyzed by X-ray diffractometry, resulting in a powder X-ray diffraction pattern which corresponds to that shown in FIG. 2 and thus indicated the preparation of predominant amounts of X-ray amorphous hemimorphite in addition to a small amount of crystalline ZnO (index card 5-0664 of the JCPDS-ICDD index(995)). The specific surface area of the resulting powder, determined according to BET, was 102.1 m$^2$/g.

EXAMPLES 9 TO 11

Catalytic reaction 650 g of the amorphous zinc silicate prepared according to Example 8 and having the composition of hemimorphite were mixed with 20.2 g of zinc stearate and precompacted to give 20 mm pellets, and subsequently comminuted to give chips having a diameter of <0.5 mm and then molded to give pellets measuring 4.75×5.2 mm. 100 g portions of each catalyst were then calcined at various temperatures for 10 hours in the air (see Table 1).

About 90 ml of th catalyst were introduced into the apparatus described above. Propyne/allene mixture (49.8% strength by volume, 2.7 mmol/min) and methanol (2.1 mmol/min; total feed with inert substances: 7.6 mmol/min; methanol/(propyne+allene) ratio=0.75) were then metered in by means of HPLC pumps. The reaction temperature was 170° C. and the pressure 1.2 bar (absolute). The results are summarized in Table 1 (abbreviations: 2MP: 2-methoxypropene; 22DMP: 2,2-dimethoxypropane; 1MP: 1-methoxypropene (cis and trans); 11 DMP: 1,1-dimethoxypropane):

TABLE 1

| Example # | Calcination °C. | Conversion Propyne/allene | Selectivity/% | | | | |
|---|---|---|---|---|---|---|---|
| | | | 2 MP | 22 DMP | Acetone | 1 MP | 11 DMP |
| 9 | 250 | 27% | 83 | 10 | 1 | 5 | 0.6 |
| 10 | 300 | 48% | 86 | 8 | 1 | 4 | 0.5 |
| 11 | 350 | 46% | 86 | 8 | 1 | 4 | 0.6 |

These catalysts have virtually no forming time. The conversions and selectivities shown in Table 1 were virtually constant from the beginning. The BET surface areas and hardnesses of the catalysts, in each case after the calcination and after removal from the reactor, are summarized in Table 2.

TABLE 2

| Example # | Calcination °C. | BET (m$^2$/g) | | Hardness (N/molding) | |
|---|---|---|---|---|---|
| | | after calcination | after removal from the reactor | after calcination | after removal from the reactor |
| 9 | 250 | 81 | 79 | 20 | 20 |
| 10 | 300 | 82 | 78 | 26 | 35 |
| 11 | 350 | 82 | 64 | 28 | 36 |

We claim:

1. A process for the preparation of compounds of the formulae I and II where R$^1$ is hydrogen or an aliphatic, cycloaliphatic, araliphatic, aromatic or heterocyclic radical or an acyl radical, it being possible for these radicals to carry further substituents which do not react with acetylenes or allenes, the radicals R, independently of one another, are hydrogen or aliphatic, cycloaliphatic, araliphatic, aromatic or heterocyclic radicals which may be bonded to one another with formation of a ring, and m is 0 or 1, by an addition reaction of a compound of the formula III

$$R^1OH \qquad\qquad III$$

with an acetylene or allene of the formula IV or V where R$^1$ and R have the abovementioned meanings, in the gas phase at elevated temperatures in the presence of a heterogeneous, silicate-containing catalyst, wherein the catalyst used is one which contains or consists of, as the active component, a zinc silicate obtainable by precipitation in aqueous solution from a soluble silicon compound and zinc compound, zinc silicate being
   a) an essentially X-ray amorphous zinc silicate of the formula VI where e is from 0 to 2a+4c and the ratio a:c is from 1 to 3.5, and the ratio f:a is from 0 to 200, and/or
   b) a crystalline zinc silicate having the structure of hemimorphite of the formula Zn$_4$Si$_2$O$_7$(OH)$_2$.H$_2$O, where zinc may be present in a 25% substoichiometric amount or 25% excess, based on the stoichiometric composition.

2. The process as claimed in claim 1, wherein the zinc silicate is X-ray amorphous and has a three-dimensional atomic structure which, using Cu-Kα$_1$ radiation (λ=1.5406 Å), gives a powder X-ray diffraction pattern (the intensity A of the diffracted X-ray is plotted as a function of twice the diffraction angle (2θ)) which, in the 2θ range from 10° to 90°, has broad intensity maxima at 31°±5° and at 61°±7°.

3. The process as claimed in claim 1, wherein the catalyst used is the hemimorphite having the composition Zn$_4$Si$_2$O$_7$(OH)$_{2-2y}$O$_y$.H$_2$O, where x and y are from 0 to 1.

4. The process as claimed in claim 1, wherein the catalyst used is one whose catalytically active component is furthermore doped with up to 80 mol % of further metals selected from the group A consisting of beryllium, magnesium, calcium, strontium, barium, manganese, iron, cobalt, nickel, copper, cadmium and mercury and from the group B consisting of titanium, zirconium, hafnium, germanium, tin and lead, the elements of group A replacing some of the zinc and the elements of group B replacing some of the silicon in the formula VI.

5. The process as claimed in claim 1, wherein the addition reaction of the hydroxyl-containing compound $R^1OH$ with the compounds of the formulae IV and V is carried out at from 100 to 350° C.

6. The process as claimed in claim 1, wherein 2-methoxypropene and/or 2,2-dimethoxypropane is prepared by an addition reaction of methanol with methylacetylene or allene at from 100 to 350° C.

7. A process for the preparation of an X-ray amorphous zinc silicate suitable for the process as claimed in claim 1, wherein an aqueous suspension of an alkali metal silicate is reacted with an aqueous solution of a zinc salt at a) from 20° C. to the boiling point of the resulting aqueous suspension, at b) a pH of from 4 to 9.5, and c) in ratios of alkali metal silicate to zinc salt such that the conditions of the formula VI are fulfilled, and d) a residence time is maintained such that considerable crystallization of the zinc silicate does not as yet occur.

8. A process as claimed in claim 5, wherein further salts of elements of group A consisting of beryllium, magnesium, calcium, strontium, barium, manganese, iron, cobalt, nickel, copper, cadmium and mercury and of group B consisting of titanium, zirconium, hafnium, germanium, tin and lead are present during the reaction in amounts of from 0 to 20 mol %, based on zinc, of group A and from 0 to 20 mol %, based on silicon, of group B.

9. An X-ray amorphous zinc silicate, comprising a) the composition corresponding to the formula VI $$Zn_aSi_cO_{a+2c-0.5e}(OH)_e \cdot fH_2O \qquad \text{VI},$$

where e is from 0 to 2a+4c and the ratio a:c is from 1 to 3.5 and the ratio f:a is from 0 to 25 and wherein b) said zinc silicate has been obtained by precipitation from an aqueous solution of an alkali metal silicate and a zinc salt at a pH of from 4 to 9.5.

10. An X-ray amorphous zinc silicate of the formula VI $$Zn_aSi_cO_{a+2c-0.5e}(OH)_e \cdot fH_2O \qquad \text{VI},$$

where e is from 0 to 2a+4c and the ratio a:c is from 1 to 3.5 and the ratio f:a is from 0 to 25, wherein said zinc silicate has a three-dimensional atomic structure which, using Cu-K$\alpha_1$ radiation ($\lambda$=1.5406 Å), gives a powder X-ray diffraction pattern (the intensity A of the diffracted X-ray is plotted as a function of twice the diffraction angle (2θ)) which, in the 2θ range of from 10° to 90°, has broad intensity maxima at 31°±5° and at 61°±7°.

11. The X-ray amorphous zinc silicate as claimed in claim 10, wherein the molar ratio of zinc to silicon is from 1.9 to 2.3.

12. A process for the preparation of a zinc silicate which is suitable for the process as claimed in claim 1 and has a hemimorphite structure, wherein an alkali metal silicate suspension is reacted with an aqueous solution of a zinc salt at atmospheric pressure and at from 50° C. to the boiling point of the resulting suspension or, under hydrothermal conditions, at from the boiling point of the suspension to 250° C., the pH of the aqueous suspension being kept in the range from 4 to 9.5 during and after the reaction and an atomic Zn/Si ratio of from 1.6 to 2.5 being maintained.

13. A process for the preparation of a zinc silicate suitable for the process as claimed in claim 1 and having the hemimorphite structure and the composition $Zn_4Si_2O_7(OH)_{2-2y}O_y \cdot xH_2O$, where x and y are each from 0 to 1, wherein zinc silicate obtainable by the process of claim 6 and having the hemimorphite structure is subjected to a thermal aftertreatment at from 70 to 600° C.

14. The process as claimed in claim 12, wherein a pH of from 5.5 to 8 is maintained.

15. The process as claimed in claim 12, wherein a pH of from 6 to 7.5 is maintained.

16. The zinc silicate having the hemimorphite structure, as obtained by the process of claim 12 or 13.

17. A process comprising an addition reaction of a hydroxyl-containing compound with acetylenes or allenes in the presence of an X-ray amorphous zinc silicate as claimed in claim 10.

* * * * *